United States Patent [19]

Green et al.

[11] Patent Number: 4,918,002
[45] Date of Patent: Apr. 17, 1990

[54] KERATINOCYTE MEGACOLONIES, AND ASSAYS FOR GROWTH FACTORS

[75] Inventors: Howard Green, Brookline; Vann Barrandon, Boston, both of Mass.

[73] Assignee: President and Fellows of Harvard College, Cambridge, Mass.

[21] Appl. No.: 898,929

[22] Filed: Aug. 21, 1986

[51] Int. Cl.$^4$ .......................... C12Q 1/02; G01N 33/48
[52] U.S. Cl. .................................... 435/29; 438/240.2; 436/63
[58] Field of Search ................... 435/29, 240.2, 244, 435/802; 436/63

[56] References Cited

U.S. PATENT DOCUMENTS

| | | | |
|---|---|---|---|
| 4,016,036 | 4/1977 | Green et al. | 195/1.8 |
| 4,304,866 | 12/1981 | Green et al. | 435/240 |
| 4,456,687 | 6/1984 | Green | 435/241 |

OTHER PUBLICATIONS

Blay et al., Biochem. J. (1985) 225, 85–94.
Blay et al., Jul. 1984, *J. of Cell. Phys.*, "Epidermal Growth Factor Promotes the Chemotactic Migration of Cultured Rat Intestinal Epitherlia Cells", vol. 124, No. 1 pp. 107–112.
Smith et al, Jun. 1985, *Nature*, "Human Transforming Growth Factor -αCauses Precocious Eyelid Opening in Newborn Mice", vol. 315 No. 6019, pp. 515–516.
Simon et al., Mar. 1985, *Cell*, "Enzymatic Cross-Linking of Involucrin and Other Proteins by Keratinocyte Particulates In Vitro", vol. 40, No. 3 pp. 677–683.
Gallico et al., Aug. 1984, *The N.E. J. of Med.*, "Permanent Coverage of Large Burn Wounds With Autologous Cultured Human Epithelium", vol. 311 No. 7, pp. 448–451.
Anzano et al., Oct. 1983, *Proc. Natl. Acad. Sci. USA*, "Sarcoma Growth Factor From Conditioned Medium of Virally Transformed Cells is Composed of Both Type $\alpha$ and Type $\beta$ Transforming Growth Factors", vol. 80 No. 19 pp. 6264–6268.
Potten, 1981 *Internatl. Rev. of Cytol*, "Cell Replacement In Epidermis (Keratopoiesis) Via Discrete Units of Proliferation", vol. 69 pp. 271–318.
Rheinwald et al., Feb. 1977, *Nature*, "Epidermal Growth Factor and the Multiplication of Cultured Human Epidermal Keratinocytes", vol. 265 No. 5593, pp. 421–424.
Withers, Mar. 1967, *Br. J. Radiol.*, "The Dose-Survival Relationship For Irradiation of Epithelial Cells of Mouse Skin", vol. 40 pp. 187–194.
Barrandon et al., Aug. 1985, *Proc. Natl. Acad. Sci.*, "Cell Size as a Determinant of the Clone-Forming Ability of Human Keratinocytes", vol. 82, pp. 5390–5394.

*Primary Examiner*—Robert J. Warden
*Assistant Examiner*—Janelle Graeter
*Attorney, Agent, or Firm*—Fish & Richardson

[57] ABSTRACT

Compounds are assayed for ability to promote epidermal cell growth and migration. The assay methods feature growing "megacolonies", which are large colonies having a surface area greater than 1 cm$^2$, and measuring growth during the linear growth phase, or measuring radial expansion during the exponential growth phase. These measurment allow comparison of growth factors and provide good estimates of the biological activity of such factors. A method of producing megacolonies and the megacolonies so produced are also disclosed.

19 Claims, 4 Drawing Sheets

FIG. 4

KERATINOCYTE MEGACOLONIES, AND ASSAYS FOR GROWTH FACTORS

BACKGROUND OF THE INVENTION

This invention relates to methods for assay of epidermal cell growth factors, in particular factors affecting keratinocyte growth and migration.

In general growth factors are chemical compounds which promote or stimulate the growth of mammalian cells in vitro and/or in vivo. Examples include epidermal growth factors (EGF's) such as the polypeptide of molecular weight 6,045 reported by Savage et al., 1972, 247 J. Biol. Chem 7612, and the α transforming growth factor (TGF-α) reported by Anzano et al., 1983, 80 Proc. Nat. Acad. Sci. 6264.

Rheinwald et al., 1977, 265 Nature 421, discloses inoculating $5 \times 10^3$ epidermal keratinocytes into a culture dish containing lethally irradiated 3T3 cells and varying amounts of EGF. The presence of EGF reportedly did not affect cell growth rate but allowed longer periods of exponential growth and resulted in larger and thinner colonies (approximately 7 mm$^2$ in surface area).

Another assay, disclosed by Smith et al. (1985, 315 Nature 515), involves injection of growth factors into newborn mice and measuring the time to eyelid opening. Growth factors such as EGF and TGF-α accelerate eyelid opening.

Anzano et al., supra, describe the formation of approximately 3,000 colonies (7,000–15,000 μm$^2$ in surface area) from NRK clone 49 F cells grown for 7 days in soft agar in the presence of TGF-α and TGF-β. They characterize such colonies as large, and rely on them as an assay for growth factors.

Keratinocytes are the principal cell type in mammalian epidermis. They can be obtained by disaggregating epidermal sections with trypsin and EDTA, as described by Rheinwald et al. (1977, 265 Nature 421). In cell culture they depend on the support of fibroblasts, such as 3T3 cells, in order to initiate colony formation. Appropriate culture media are described by Simon et al. (1985, 40 Cell 677) and Rheinwald et al., supra.

SUMMARY OF THE INVENTION

In general, the invention features methods for assaying compounds for their ability to promote epidermal cell growth and migration. This ability provides a biological model for wound healing and therefore it can be used as assay for factors that aid or accelerate wound healing.

We have discovered that it is possible to grow large colonies ("megacolonies" as defined below) which undergo an exponential and then a linear growth phase. During the exponential phase it is possible to measure cellular migration rates relatively free from cell growth; and during the linear phase it is possible to measure growth rate. We have found that these measurements can be used to assay for potential growth factors and to compare one growth factor with another.

A megacolony, for purposes of the invention, is a colony formed in a medium from a single keratinocyte cell, or small group of closely placed cells, which contains more than about $2 \times 10^5$ cells, and has a surface area of at least 1 cm$^2$. A megacolony is distinguished from a colony in that it is substantially larger than a colony (e.g. nearly an order of magnitude).

In one aspect, the assay features including the compound to be assayed for ability to promote epidermal cell growth and migration, in a medium which will allow megacolony formation, placing a keratinocyte cell into the medium, incubating the keratinocyte cell to allow megacolony formation, and observing the formation of a megacolony. Formation of a megacolony is indicative that the compound induces cell growth and migration.

In preferred embodiments the assay includes measuring the rate of radial expansion of the megacolony, preferably during the linear growth phase or after 12 days of incubation of the keratinocyte cell. This measurement allows direct comparison of one compound with another, the greater the growth and migration rates are, the more likely the compound is to be useful in wound healing. Preferably, the culture is started from only one keratinocyte cell, but if more than one is used then it is placed at least 2 cm, and preferably 5 cm from all other keratinocyte cells. The cells are preferably grown in a 10% CO$_2$ atmosphere at 36°–37° C., with gentle rocking of the medium, sufficient to aid dispersion of the medium but not to disrupt the colony.

In a second aspect the method of the invention features growing a keratinocyte cell to form a colony in medium that will allow colony formation but not megacolony formation from the keratinocyte cell. Once the colony is formed, a test compound is added to the medium and, after a period substantially less than the doubling time of cells in the colony, the resulting increase in colony diameter is measured, whereby the increase is attributable to the ability of the compound to induce cell migration.

In preferred embodiments the colony is in exponential phase or is 4–9 days old when the percentage increase in area of the colony is measured, preferably multiple times, within 3 hours after the compound is added to the medium.

The invention also features a method for growing a megacolony and the megacolony itself. Preferably the megacolony is formed from an epidermal keratinocyte.

The method is useful for assaying unknown compounds for their ability to aid in wound healing. The assay methods provide an improved model for the natural wound healing system, and therefore they are useful for assaying unknown compounds for their ability to aid in wound healing. At present assays for wound healing factors involve burning the skin from pigs and testing various compounds for their ability to enhance wound healing. The new assay allows a carefully controlled, reproducible, rapid, and quantitative comparison of any number of compounds. Those compounds which induce the greatest rate of linear growth of megacolonies and which produce the greatest increase in cell mobility are the most likely to be useful as wound healing agents.

Other features and advantages of the invention will be apparent from the following description of the preferred embodiments therefrom, and from the claims.

DESCRIPTION OF THE PREFERRED EMBODIMENTS

The figures will first briefly be described.

DRAWINGS

STRUCTURE

Keratinocytes

Keratinocytes can be derived from any mammal (preferably human) and cultured b standard techniques. Preferably the keratinocytes are derived from mammalian epidermis. When used for megacolony formation (see below) they are preferably small in size (10-16 μM, but can be up to 21 μM) so that they give rise to colonies with high frequency. Such keratinocytes are preferably freshly isolated from an animal tissue, or isolated from frozen cell cultures at an early passage, and have been subcultured fewer than twelve times, more preferably fewer than five times. Cells which have been cultured more than this generally will not respond to growth factors in the manner described below, although it is possible that certain cell lines do work, e.g. human squamous carcinoma cell lines.

Megacolonies

Megacolonies are colonies formed in medium from a small group of cells, preferably only one cell, placed at one position (i.e. within an area of less than 1 mm$^2$) in a culture vessel. If more than one cell is used then the results from the assay of the invention (see below) will be less reliable, since growth rate of the resulting megacolony may be less well controlled. Similarly if cells are placed at more than one position in the culture vessel then two or more megacolonies may form and fuse, influencing one another's diameter and making it difficult to measure the appropriate colony parameters (see below). Further, the cell must be positioned in the culture vessel, such that the expansion of the megacolony formed is not impeded by any physical barrier, such as a flask wall, or other colonies or megacolonies. These megacolonies contain more than $2 \times 10^5$ cells, and their surface area exceeds 1 cm$^2$ in size, below this size the cell mass is termed a colony. Megacolonies can only be grown in medium having at least one growth factor. Their growth rate is exponential for about 7 days, at which point it becomes linear. Since the megacolonies are grown from a single cell positioned at a distance (preferably 5 cm) from other colonies, the growth of a megacolony is readily followed by repeated measurements over time, even after a substantial period (e.g. 5-18 days) of linear growth. The megacolony is further characterized by having a well defined perimeter consisting essentially of a monolayer of dividing cells; the megacolony thus lacks the scalloping pattern characteristic of a film grown from a plurality of overlapping colonies.

Methods

In general the assay methods of the invention provide a biological assay for wound healing ability since they involve the use of culture systems which imitate the behavior of cells, especially keratinocytes, in the epidermis. That is, when the epidermis is wounded cells migrate out from an intact portion of the epidermis, or from adnexal structures beneath the wounded epidermis, and begin to grow rapidly—thus repairing the wound. In the culture systems of the invention single cells or groups of cells, are isolated and placed at one location in separate dishes containing irradiated 3T3 cells. This location is chosen so that the cells may grow unimpeded by the walls of the dish or by other colonies in the dish. These single cells grow into colonies (generally about 50 mm$^2$ or less and certainly less that 1 cm$^2$ in surface area) and single cells from such colonies can be used for further colony formation. After a colony reaches a certain size (greater than 1 cm$^2$ in surface area) it is termed a megacolony and it enters a phase of linear growth, the rate of which is dependent upon the presence of growth factors and upon the rate of outward cell migration at the periphery of the colony. This migration rate can be readily measured within minutes, while linear growth rate can be measured over days. The dependence of the cells in a megacolony on such growth factors resembles that of epidermal cells in a healing wound. Thus, the culture systems represent suitable models for testing the use of a growth factor for its wound healing ability and for comparing different growth factors.

EXAMPLE 1

Megacolony formation

In order to demonstrate megacolony formation human epidermal keratinocytes, derived from the foreskin of seven newborn humans, were cultivated as described by Rheinwald et al., supra, or used directly. Cells obtained after trypsinization (0.1% trypsin from NEC Labs, for 30 mins. at 37° C.) of either fresh epidermis or cultures were centrifuged and resuspended in medium (see below). Cells (500-1000) in 8-10 ml medium were placed in a 100 mm dish, and observed under a Zeiss IM35 photo-invertoscope with x10 phase objective. A single randomly selected cell wa aspirated and inoculated into a culture dish (35 or 60 mm Petri dish) containing lethally irradiated 3T3 cells, and a 3:1 mixture of the Dulbecco-Vogt modified Eagle's medium and Ham's F-12 medium (Ham, 1965, 53 Proc. Nat. Acad. Sci. 288), supplemented with 10% fetal calf serum; 0.4 μg/ml hydrocortisone, 5 μg/ml insulin, 5 μg/ml transferrin, $2 \times 10^{-9}$M triodothyronine, $10^{-10}$M choleragen and $1.8 \times 10^{-4}$M adenine (Simon et al., 1985, 40 Cell 677). All cultures were incubated at 36°-37° C. in a 10% CO$_2$ atmosphere. Mouse EGF (isolated as described in Savage et al., supra) was added at 4 days, and every 4th day, at 10ng/ml. The medium was changed every 4th day. Colonies were visible by about 6 days after inoculation (growth rate being exponential up to about 8 days) and increased in size for more than 20 days. By 14 days satellite colonies were commonly observed; these were much smaller than the principal colony. Satellite colonies arise through cell displacement from the principal colony.

By 16-28 days the colonies were megacolonies, being greater than 1 cm$^2$ in surface area and containing about $2 \times 10^5$ cells. Colony size continued to increase up to 29 days of incubation. Colony size of 5-10-day-old colonies was measured by microscopic photography of the colony, tracing its outline onto paper and weighing the paper. The area was corrected for microscopic and photographic magnification. Areas of 10 to 29-day-old colonies were measured without enlargement. A Petri dish containing a colony was placed over paper ruled in mm, and the area determined by counting the number of squares with the colony. The cell number in a colony was obtained by trypsinizing the colony and counting;

the number of cells was proportional to the area of the colony (1800 cells/mm$^2$).

EXAMPLE 2

Effect of Rocking on Megacolonies

Human epidermal keratinocytes were grown in the presence of lethally irradiated 3T3 cells using the medium and growth conditions described above. The keratinocytes were inoculated individually into 25 cm$^3$ flasks and after 6 days placed on a commercial platform rocker (Bellco Corp.) set to 9 oscillations/minute. Growth factor (30 ng/ml) was added on day 6, and every 3 days thereafter, when the medium was changed. This rocking stimulated colony growth in the presence of growth factors, as shown in the table below.

| | Area of Colonies (mm$^2$) | | | |
| --- | --- | --- | --- | --- |
| | No EGF | | +EGF (10 ng/ml) | |
| Day | Stationary | Rocked | Stationary | Rocked |
| 6 | 0.150 | 0.108 | 0.188 | 0.191 |
| 8 | 0.497 | 0.419 | 1.06 | 1.18 |
| 10 | 1.97 | 1.87 | 3.84 | 4.66 |
| 12 | 5.30 | 5.71 | 18.1 | 24.8 |
| 14 | 13.9 | 14.8 | 44.8 | 65.0 |
| 16 | 24.1 | 20.3 | 92 | 148 |
| 20 | 35.8 | 30.4 | 248 | 401 |

In the absence of human EGF (obtained from Chiron, San Francisco, CA) rocking had little effect on the rate of colony growth. In the presence of EGF, beginning at about 7 days after inoculation, colonies in the rocked samples grew more rapidly than those in stationary flasks. By 16 days, the colonies were 50% larger with rocking. This effect is not caused by oxygen but is presumably related to some diffusion-limited transfer.

EXAMPLE 3

Linear Growth Rate of Megacolonies

Figure 1:
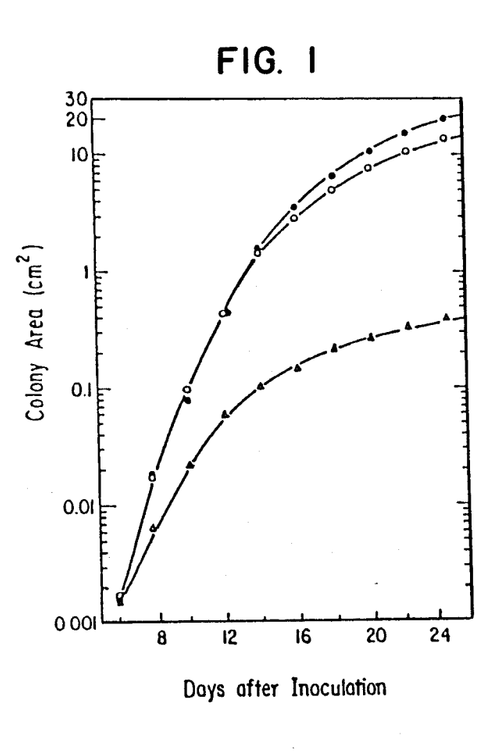
FIG. 1 is a graphical representation of the effect of growth factors on megacolony formation.

Referring to FIG. 1, single cells were isolated from an 8 day old clone and carefully deposited onto the center of a 150 cm$^3$ flask, containing lethally irradiated 3T3 cells. The flasks were allowed to stand for 30–45 min, to permit attachment of the cells, before being moved to the incubator. In order to conserve the growth factors, and since EGF was known to have no effect on the growth rate of very small colonies (Rheinwald et al., supra), addition of the growth factors to the medium was begun on the 6th day. Area measurements were made as described above, using an image analyzing system (Microplan II, Nikon), without disturbing the growing colonies. Each point is the mean of 9 or 10 colonies formed by sister cells. Open triangles, no growth factor added; open circles, human EGF (Urdea et al., 1983), was added to 30 ng/ml at each feeding; solid circles, human TGF$_\alpha$ (obtained from Genentech, San Francisco, Calif.), was added to the same concentration (in EGF equivalents), as determined by receptor binding assay (Derynck et al., 1984). In all experiments the cultures were rocked beginning 6 days after inoculation.

Since different colonies may have different growth potential the founding cells for the entire experiment on the effects of the growth factors were derived from a single colony. This resulted in very uniform growth of the 9 or 10 colonies in each group. As reported earlier (Rheinwald et al. supra), colony growth is independent of EGF as long as the colony is very small. By 8–10 days, the effects of both EGF and TGF$_\alpha$ became appreciable. By 13 days, colonies grown in the presence of TGF$_\alpha$ were 10 times larger than in its absence, and by 24 days, 50 times larger. It is only after 12–14 days (colony size approaching 1–2 cm$^2$) that linear growth of the colonies is evident, and only at this point can the different effects of EGF and TGF$_\alpha$ be readily discerned.

Figure 2A:
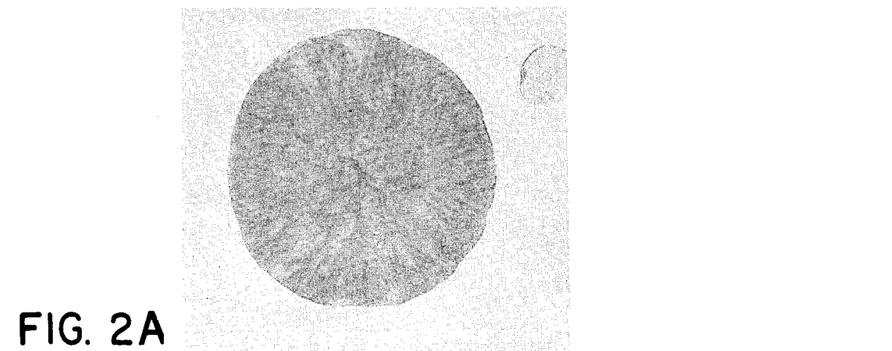
FIG. 2 is a photograph of colonies grown in the presence (A and B) or absence (C) of growth factors.
Figure 2B:
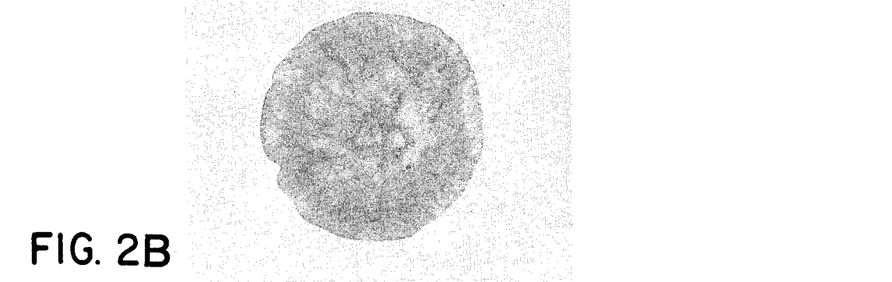
Figure 2C:
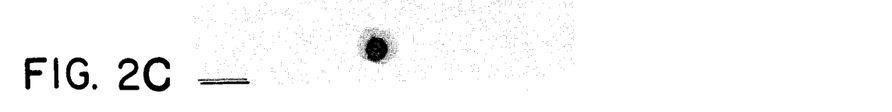

Referring to FIG. 2, a colony grown under each condition in the experiment of FIG. 1 was fixed at 24 days and stained with rhodamine. Photograph A, with TGF$_\alpha$, the principal colony has an area of 22.2 cm$^2$, and contains about $4 \times 10^6$ cells; photograph B, with EGF (colony Area=15.5 cm$^2$); photograph C, with neither growth factor (colony Area=0.47 cm$^2$). The bar in the figure indicates 1 cm. The small satellite colony in photograph A is the result of cell detachment from the principal colony during the experiment. In the absence of both factors, epidermal cells were unable to grow into a megacolony.

Figure 3:
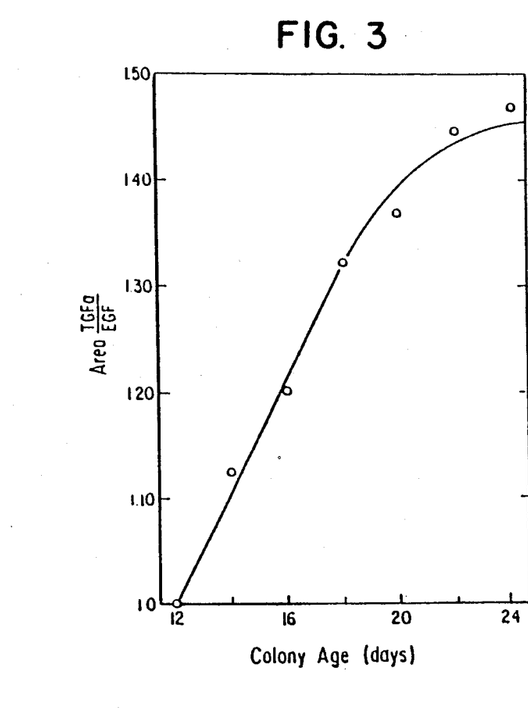
FIG. 3 is a graphical representation of the relative effect of TGF-α and EGF on colony growth.

Referring to FIG. 3, in a group of 3 experiments, the effect of TGF$_\alpha$ was always more powerful than that of EGF, but the difference between the two polypeptides did not appear until the colonies reached 14 days of age. At 24 days, the colonies grown in the presence of TGF$_\alpha$ were larger by 45% (FIGS. 2 and 3). The greater effect of TGF$_\alpha$ was observed at all concentrations between 1 and 100 ng/ml, the saturating concentration for both agents being 10–30 ng/ml.

EXAMPLE 4

Cell migration in megacolonies

Figure 4:
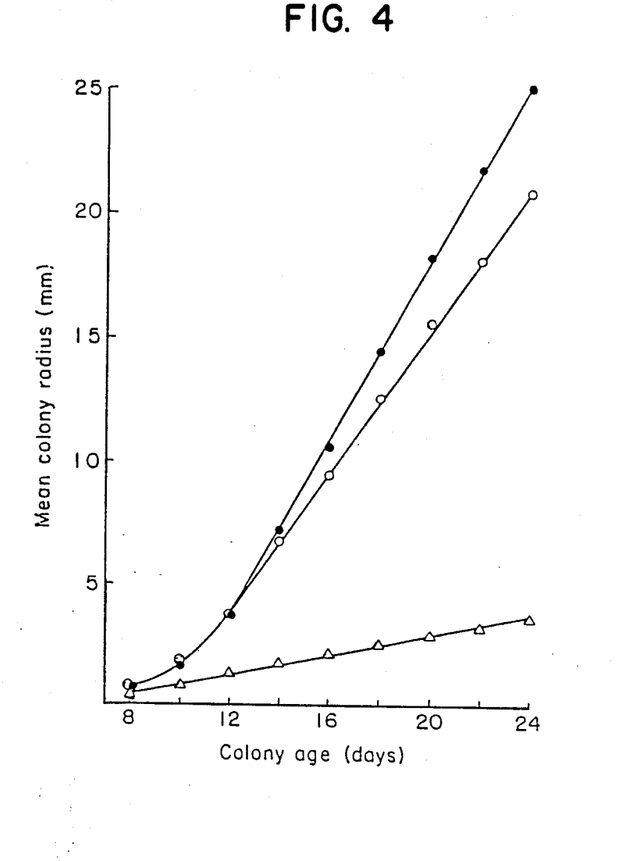
FIG. 4 is a graphical representation of the growth rate of colonies.

Referring to FIG. 4, after 8 days, each keratinocyte colony consists of a stratified epithelium whose cells are no longer able to maintain exponential growth. In order that cells generated by multiplication in the basal layer remain in that layer and continue to multiply, they must migrate centrifugally at the perimeter of the colony. After the colony becomes 8–12 days old, it enters a phase of linear growth, in which its radius increases at a constant rate. This rate is 0.15 mm/day in the absence of growth factors (open triangles), 1.42 mm/day in the presence of EGF (open circles), and 1.79 mm/day in the presence of TGF$_\alpha$ (solid circles). The multiplying population must consist mainly of cells that have migrated across the width of the active zone, a migration distance which, in the presence of TGF$_\alpha$, is equal to about 70 cell diameters.

Figure 5:
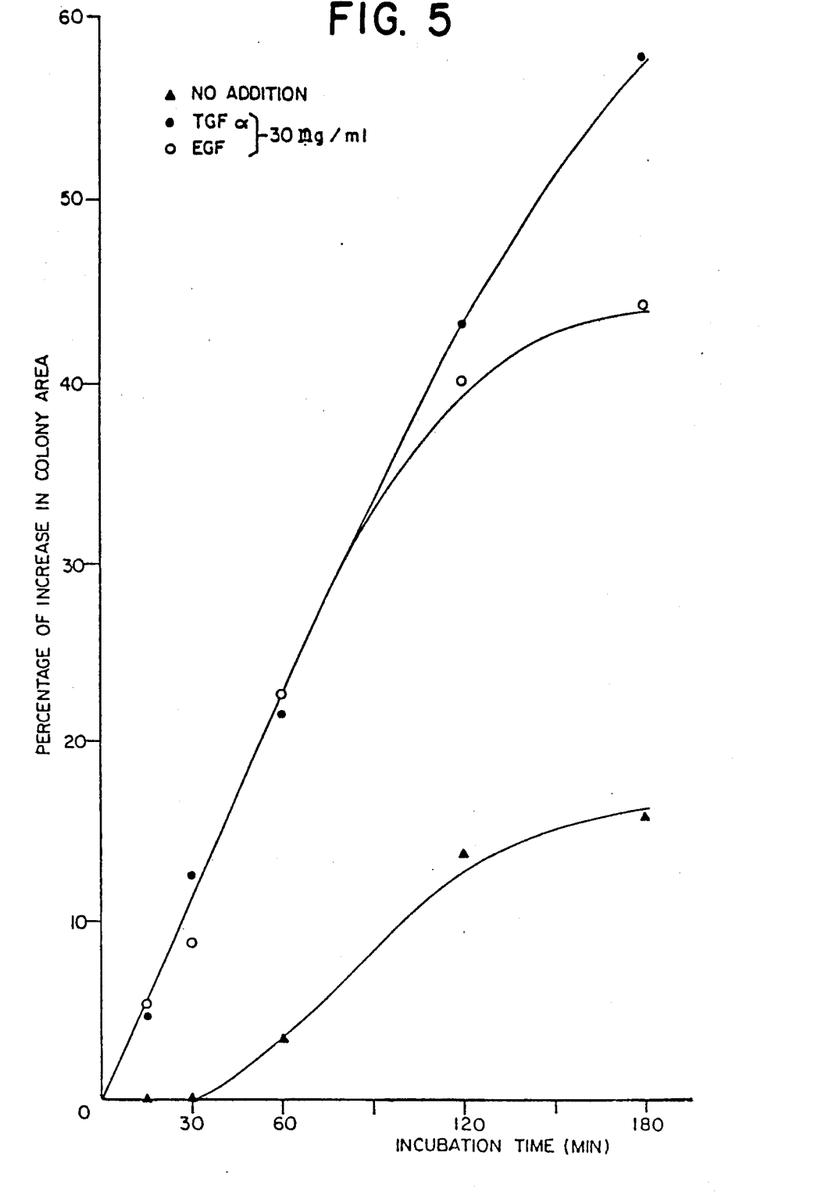
FIG. 5 is a graphical representation of the percent increase in colony area after treatment with (circles) or without (triangles) a growth factor.

A colony growing in the absence of the growth factors contains closely packed cells which begin to stratify rather early. Referring to FIG. 5, within 15 min of the addition of 30 ng/ml TGF$_\alpha$ (solid circles) or EGF (open circles) to cultures (in triplicate) containing a 7 day colony, an effect can be observed on cell migration, measured by increase in colony radius. The control, having no addition of growth factors is shown as solid triangles. The cells begin to move centrifugally, and the cell density in the center of the colony becomes reduced. After 2–3 hours of addition the difference between TGF$_\alpha$ and EGF can be observed. The greater increase in colony radius is caused by increased cell migration (note that cell doubling time is 17–18 h). TGF$_\alpha$ has a greater effect, than does EGF, on cell migration.

Use

In the healing of epidermal wounds, cells must be able to migrate. Proliferating cells may originate in the basal layer outside the wounded area or in the adnexal structures beneath the wounded basal layer. The perimeter of a megacolony resembles a wound edge since it separates a large zone of closely packed epidermal cells, with low growth rate, from a zone to be covered by cell migration and proliferation. Accordingly, megacolonies should reveal the effects of any factors affecting cell migration and multiplication in the skin with greater sensitivity than the small colonies commonly grown in culture.

Both EGF and $TGF_\alpha$ promote epithelial wound healing in animal experiments. All other things being equal, the greater the colony diameter, the greater the ability to heal wounds. The above described culture systems are well suited for investigation and comparison of the properties of $TGF_\alpha$ and other growth factors. The assays of the invention are suitable assays for biological activity of growth factors and for distinguishing between such factors. This is particularly evident when one considers that EGF and TGF-$\alpha$ are very similar in that they recognize the same cell receptor, and yet could be distinguished and compared in the assays of the invention.

Other embodiments are within the following claims.

We claim:

1. A method for qualitatively assaying a compound for ability to promote epidermal cell growth and migration, comprising the steps of:
    including said compound in a medium which, without said compound, will allow colony formation from a keratinocyte cell but will not alone allow megacolony formation from said cell,
    placing a said keratinocyte cell at a position in said medium,
    incubating said keratinocyte cell and said medium,
    and determining whether a megacolony is formed, said megacolony having a surface area of at least 1 $cm^2$ and containing at least $2 \times 10^5$ cells,
    wherein formation of said megacolony indicates that said compound promotes cell growth and migration.

2. The method of claim 1 further comprising measuring the rate of radial expansion of said megacolony over time.

3. The method of claim 2 wherein said measuring comprises measuring said expansion during linear growth of said megacolony.

4. The method of claim 2 wherein said measuring is performed after twelve days of incubation of said keratinocyte cell.

5. The method of claim 1 wherein said colony is grown from only one said keratinocyte cell.

6. The method of claim 1 wherein said keratinocyte cell is positioned at least two cm from any other said keratinocyte cell.

7. The method of claim 1 wherein said keratinocyte cell is positioned at least 5 cm from any other said keratinocyte cell.

8. The method of claim 1 wherein said incubating is in 10% $CO_2$ and at 36°–37° C.

9. The method of claim 1 wherein said incubating comprises gently rocking said medium.

10. A method of quantitatively assaying a compound for the ability to promote epidermal cell migration, comprising the steps of:
    growing a keratinocyte cell to form a colony at a position in a medium which will allow said colony formation from said cell but will not alone allow formation from said cell of a megacolony having a surface area of at least 1 $cm^2$ and containing at least $2 \times 10^5$ cells,
    adding said compound to said medium,
    measuring increase in said colony diameter after a period substantially less than the doubling time of cells in said colony, and
    comparing said increase with that observed in a colony grown without adding said compound, whereby said increase is attributable to the ability of said compound to induce cell migration.

11. The method of claim 10 wherein said colony is in exponential growth phase at the time of said adding.

12. The method of claim 11 wherein said colony is 4–9 days old at the time of said adding.

13. The method of claim 10 wherein said measuring comprises measuring the percentage increase in area of said colony.

14. The method of claim 10 wherein said at least one said measuring step is performed within 3 hours after said adding step.

15. The method of claim 10 wherein said colony is grown from only one said keratinocyte cell placed in said medium.

16. The method of claim 10 wherein said keratinocyte cell is positioned at least two cm from any other said keratinocyte cell 17. The method of claim 10 wherein said keratinocyte cell is positioned at least 5 cm from any other said keratinocyte cell.

18. The method of claim 10 wherein said growing is in $CO_2$ and at 36°–37° C.

19. The method of claim 10 wherein said growing comprises gently rocking said medium.

* * * * *

UNITED STATES PATENT AND TRADEMARK OFFICE
CERTIFICATE OF CORRECTION

PATENT NO. : 4,918,002

DATED : April 17, 1990

INVENTOR(S) : Green et al.

It is certified that error appears in the above-identified patent and that said Letters Patent is hereby corrected as shown below:

Title page:

In the "[75] Inventors:" section "Vann" should be --Yann--.

Signed and Sealed this

Third Day of September, 1991

Attest:

HARRY F. MANBECK, JR.

*Attesting Officer* — *Commissioner of Patents and Trademarks*

UNITED STATES PATENT AND TRADEMARK OFFICE
CERTIFICATE OF CORRECTION

PATENT NO. : 4,918,002
DATED : April 17, 1990
INVENTOR(S) : Howard Green et al.

It is certified that error appears in the above-identified patent and that said Letters Patent is hereby corrected as shown below:

Column 1, line 4, immediately before the first full paragraph of the Background section, please add the following paragraph:

--This invention was made at least in part with funds from the United States Government including funds under NIH Grant 5-R01-GM33158. The Government has certain rights in the invention.--

Signed and Sealed this

Nineteenth Day of May, 1992

Attest:

DOUGLAS B. COMER

Attesting Officer

Acting Commissioner of Patents and Trademarks